United States Patent [19]
Willis

[11] Patent Number: 5,433,742
[45] Date of Patent: Jul. 18, 1995

[54] CONDUCTIVE ADHESIVE BAND FOR CATHETHER ELECTRODE

[76] Inventor: Allan Willis, 12440 Alderglen St., Moorpark, Calif. 93021

[21] Appl. No.: 154,982

[22] Filed: Nov. 19, 1993

[51] Int. Cl.⁶ ............................................. A61N 1/05
[52] U.S. Cl. ................................... 607/122; 607/116
[58] Field of Search ............... 607/115, 116, 119, 122, 607/124; 128/642

[56] References Cited

U.S. PATENT DOCUMENTS

| | | |
|---|---|---|
| 3,543,759 | 12/1970 | McWhorter . |
| 3,731,376 | 5/1973 | Ackerman . |
| 3,995,623 | 12/1976 | Blake et al. . |
| 4,519,403 | 5/1985 | Dickhudt . |
| 4,637,404 | 1/1987 | Gessman . |
| 4,785,823 | 11/1988 | Eggers et al. . |
| 5,029,585 | 7/1991 | Lieber et al. . |
| 5,061,267 | 10/1991 | Zeiher . |
| 5,069,215 | 12/1991 | Jadvar et al. ............... 607/124 |
| 5,156,151 | 10/1992 | Imran . |
| 5,199,433 | 4/1993 | Metzger et al. ............... 607/124 |
| 5,201,754 | 4/1993 | Crittenden et al. . |
| 5,211,631 | 5/1993 | Sheaff . |

FOREIGN PATENT DOCUMENTS 0363117  4/1990  European Pat. Off. .
8912421 12/1989  WIPO .

OTHER PUBLICATIONS

*Flow-Directed Thermal-Dilution Optical Pulmonary Artery Catheter Series D Model P7110*, Opticath Optical Pulmonary Artery Catheter, product information.

Primary Examiner—William E. Kamm
Assistant Examiner—Kennedy J. Schaetzle
Attorney, Agent, or Firm—Knobbe, Martens, Olson & Bear

[57] ABSTRACT

The present invention provides a novel cardiac catheter comprising adhesive band electrodes and a method of making the bands for the electrodes. The conductive adhesive band electrodes are easy to manufacture, produce predictable results, and improve the uniformity of the flexibility characteristics of the catheter.

7 Claims, 5 Drawing Sheets

CONDUCTIVE ADHESIVE BAND FOR CATHETHER ELECTRODE

FIELD OF THE INVENTION

The present invention relates to cardiac catheters and, in particular, to a conductive adhesive band for the pacing electrodes of the catheter and to the method of making the band for the electrodes.

BACKGROUND OF THE INVENTION

Conventional pacing cardiac catheters employ electrodes located along the distal length of the catheter. The electrodes are extrinsically mounted onto the catheter and are typically comprised of metal bands or tubes. The leads or wires extend from the electrodes, proximally through the flexible tubing member of the catheter, and are connected to an electrical apparatus used to perform diagnostic or therapeutic electrical functions with respect to the electrodes.

The electrodes located on the catheter are typically used either to accurately measure the electrical potentials in the walls forming the chambers of the heart or to pulse electrical current to stimulate the heart. The catheter is inserted through a small incision in a vein or artery of the patient. It is then passed along the blood vessel and into the heart. Once the catheter is properly positioned within the heart, electrical activity within the heart may be regulated or monitored via the electrodes located on the catheter.

Disadvantages associated with conventional cardiac pacing catheters include difficulties in securely attaching them and the costs associated with effectively mounting the metal bands on the tubular body. The metal band electrodes have been known to become loose and slide off of the tip of the catheter and remain in the patient. In addition, since the metal bands are located on the exterior surface of the catheter's flexible tubing, there is a greater likelihood of the band becoming snagged or scraping the internal surface of the patient's blood vessel or heart. This trauma to the vascular intima may lead to arrythmia and/or fibrillation of the heart. Therefore, there is a need for a cardiac catheter comprising electrodes which are easy to manufacture and which solve the above mentioned disadvantages associated with conventional cardiac catheters.

SUMMARY OF THE INVENTION

The present invention relates to cardiac catheters and, in particular, to cardiac catheters comprising adhesive band electrodes and to the method of making the bands for the electrodes. The application of the conductive adhesive band electrodes of the present invention simplifies the construction method, produces more predictable results, and improves uniformity of the flexibility characteristics of the catheter.

The cardiac catheter comprises an elongate tubular body, which connects at its proximal end to a pigtail sheath. Housed within the lumen of the tubular body are wires, tubes and optical fibers which protrude out the proximal end of the pigtail sheath and connect to various medical instruments and equipment. The tubes, wires and optical fibers are used to inflate balloons, inject medication into the patient, monitor characteristic intraarterial and intraventricular signals, generate a pacemaker pulse, measure a patient's core temperature, etc, as desired for a particular application.

The manner by which the intraarterial and intraventricular signals are monitored and the pacemaker pulse is generated is via one or more electrodes located on the catheter body. The tubular body of the catheter, comprising electrodes, is inserted into the veins or arteries of a patient and advanced to the chambers of the heart. The electrodes are then properly located against the walls of the heart so that the electric potentials in the walls forming the chambers of the heart can be monitored. In addition, if the patient suffers cardiac arrest during the above mentioned procedure, the pacing electrodes are also able to deliver the appropriate electrical therapy to the heart.

The electrodes located on the catheter comprise electrode bands, which are applied to the exterior surface of the catheter body as an adhesive conductive layer rather than as a preformed metal band. The conductive layer may be masked and sprayed, brushed, dipped or otherwise applied to the surface of the catheter body. Prior to the application of the conductive layer, the catheter body is provided with an exposed electrical contact (i.e., un-insulated wire) in the location of the electrode band for electrically communicating with the conductive layer.

The conductive adhesive electrode bands present a relatively smooth external surface which is substantially continuous with the external surface of the catheter. Thus, there are no sharp edges on the electrode bands which could snag or scrape against the walls of an artery, a vein, or a patient's heart and, possibly, become detached from the catheter.

The present invention is specifically designed to overcome certain disadvantages associated with traditional cardiac catheters. By applying the conductive adhesive band electrodes to the outer surface of the catheter, the problems associated with snagging or detached electrodes are minimized. Thus, the present invention simplifies the method of constructing catheter electrodes, produces more predictable results, and improves uniformity of the flexibility characteristics of the catheter.

DETAILED DESCRIPTION OF THE PREFERRED EMBODIMENTS

Figure 1:
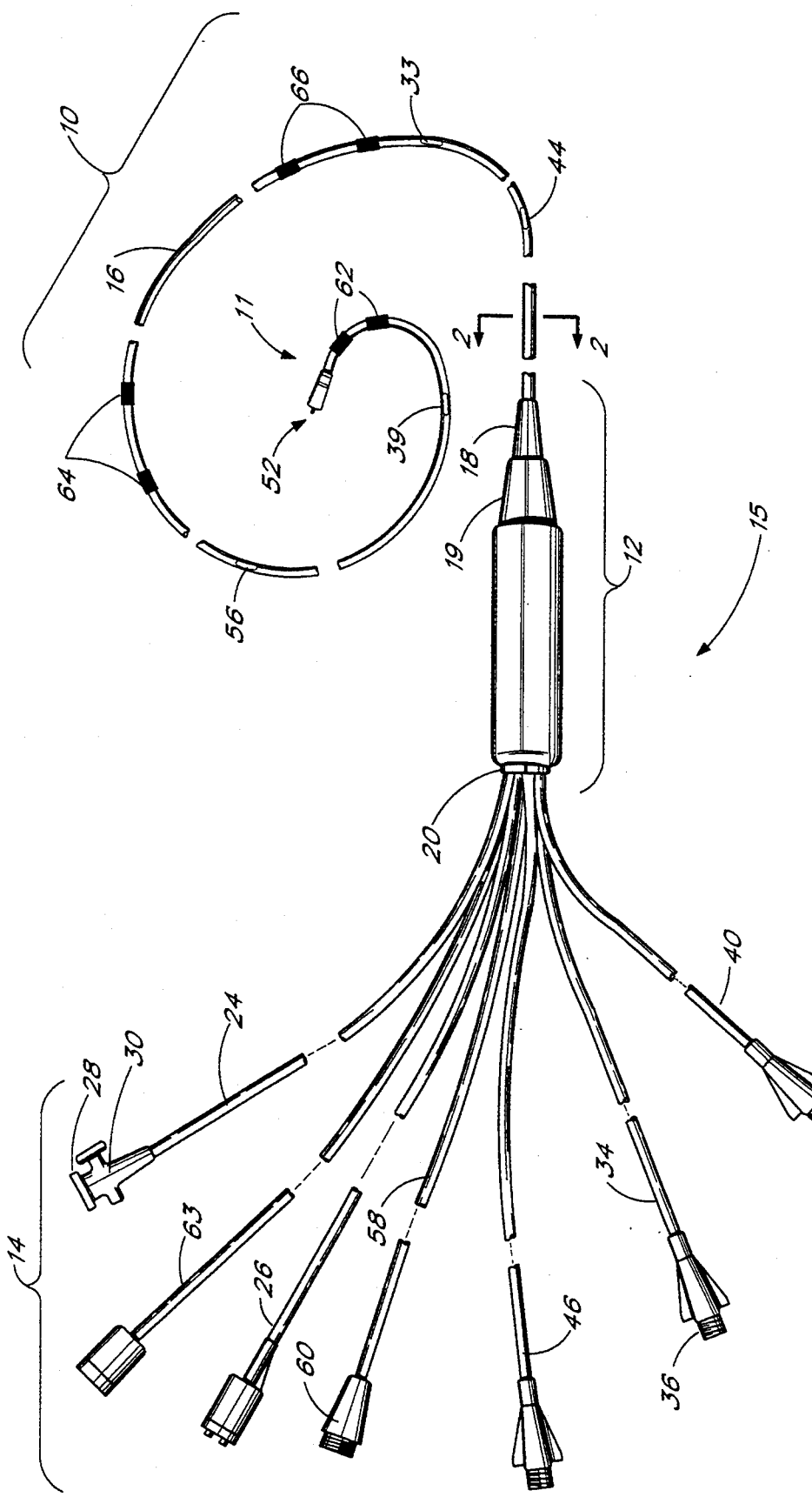
FIG. 1 is a plan view of a cardiac catheter illustrating the tubes, wires and optic fibers.

Referring to FIG. 1, there is shown a cardiac catheter 15 of the present invention comprising a distal portion 10, a pigtail sheath 12, and a proximal portion 14. The distal portion 10 of the cardiac catheter 15 comprises an elongate flexible tubular body 16, which connects at its proximal end 18 to the distal end 19 of a pigtail sheath 12. Although the present disclosure will describe the electrodes of the present invention in the context of a multifunctional cardiac catheter, it is to be understood that the electrodes can also readily be used with simplified catheters having more limited capabilities.

Cardiac catheters generally are capable of performing a variety of functions. As a consequence, the tubular body 16 is generally provided with a plurality of lumen extending axially therethrough to accommodate the various conductors, fiber optics, inflation fluids and others as needed for a particular catheter design. For example, the wires 50 and optical fibers 52 housed within the distal portion 10 of the catheter 15 generally extend through one or more axially extending lumen, as shown in FIG. 2.

A balloon inflation lumen 22 is also provided, for permitting fluid communication between an inflatable balloon 23 in the tubular body 16 and the distal end 19 of the pigtail sheath 12. The inflatable balloon 23 is located at the distal end 11 of the tubular body 16 and inflates via the balloon inflation lumen 22.

The inflation lumen 22 extends proximally through the pigtail sheath 12 and communicates with an inflation tube 24 at the proximal end 20 of the pigtail sheath 12. In use, the inflation tube 24 is connected at its proximal end 28 to an air or liquid inflation source (not shown). The inflation tube 24 may be made from Polyvinyl Chloride (PVC) or Polyurethane (PU) or other known materials, and is generally flexible, with 80–100 durometer, shore A. The inflation tube 24, including a proximal fitting 30 used to connect the tube 24 to the air source (not shown), is typically about 16 cm in length. The balloon lumen 22 is used to distend or maintain an opening in an internal cavity via inflation of the balloon.

Figure 2:
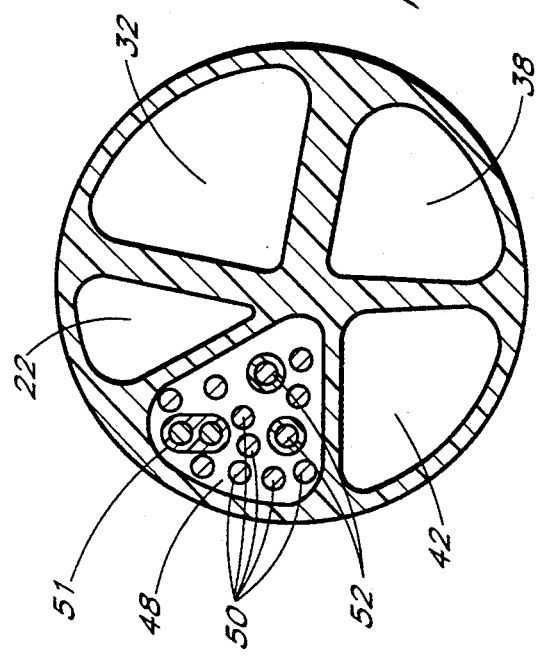
FIG. 2 is a cross section taken along the line 2—2 of FIG. 1 illustrating the components inside a lumen of the cardiac catheter.

Referring to FIGS. 1 and 2, a second lumen 32, located adjacent the balloon lumen 22, comprises a hollow through-area extending between an opening or port 33 near a proximal end 18 of the tubular body 16 and the distal end 19 of the pigtail sheath 12. A proximal extension tube 34 is connected to the proximal end 20 of the pigtail sheath 12, and is in fluid communication with the second lumen 32.

In use, the proximal end 36 of tube 34 is typically connected to a syringe filled with of bolus of chilled saline or glucose (not shown), used for CO measurements. In another embodiment, the proximal extension tube 34 may be connected to a syringe used to infuse and sample fluids, such as blood, and to measure cardiac output. The proximal extension tube 34 is typically 10 cm in length and is fabricated from PVC or PU, with 80–100 durometer, shore A.

A third lumen 38, located adjacent to the second lumen 32, is typically also provided. Third lumen 38 comprises a hollow through-area extending between an opening or port 56 located along the distal portion 11 of the flexible body 16 and the distal end 19 of the pigtail sheath 12. An extension tube 40 is in fluid communication with the third lumen 38 by way of the proximal end 20 of the pigtail sheath 12.

In use, the extension tube 40 is typically connected to an external transducer (not shown) and is used to monitor pressure. In another embodiment, the extension tube 40 may be connected to a syringe to infuse samples or withdraw blood. In yet another embodiment, the extension tube 40 may be used as a means of guiding the catheter 15 by passing a guidewire through the hollow through-area of the tubular body 16 and the flexible extension tube 40. The extension tube 40 is typically 12 cm in length.

Adjacent the third lumen 38 is a medication lumen 42. The medication lumen 42 comprises a hollow through-area extending between an opening or port 44 located along the tubular body 16 and the distal end 19 of the pigtail sheath 12. A medication extension tube 46 is in fluid communication with the medication lumen 42 by way of the proximal end 20 of the pigtail sheath 12.

In use, the medication extension tube 46 is typically connected to bottles or bags (not shown) containing the necessary medication used for diagnosis or treatment of the patient. Although FIG. 1 shows one medication port 44 located near the proximal portion 18 of the tubular body 16, other embodiments comprising a plurality of ports in various locations along the tubular body 16 are also possible. These alternate embodiments of the present invention allow greater volumes of medication to be delivered in a shorter period of time and/or in a variety of locations. The medication extension tube 46 is typically 14 cm in length. The extension tube 40 and the medication extension tube 46 are typically manufactured from flexible PVC or PU, with 80–100 durometer, shore A.

An additional lumen 48, as shown in FIG. 2, comprises a hollow through-area extending between the distal end 11 of the tubular body 16 and the distal end 19 of the pigtail sheath 12. Housed within the lumen 48 are any of a variety of conductors or wires 50 and optical fibers 52 depending upon the desired application of the catheter. The wires 50 and optical fibers 52 extend out the proximal portion 20 of the pigtail sheath 12 for connection to various medical instruments used for patient diagnosis, monitoring and treatment.

The fiber optic bundle housed within the lumen 48 is used to measure the oxygenated fraction of hemoglobin through the transmission and reception of light as is known in the art. The optical fibers 52 extend from the distal end 11 of the tubular body 16 to the distal end 19 of the pigtail sheath 12. An optical extension tube 26 houses the optical fibers 52 at the proximal end 20 of the pigtail sheath 12.

The fiber optic bundle typically comprises 2–3 fibers 52 which transmit light to the blood and gather the light reflected from the blood. As the blood flows past the tip 54 of the catheter 15, a predetermined wavelength of light is transmitted to the blood. Some of the light is reflected back and collected at the tip 54 of the catheter 15. Due to differences in absorption of oxygenated and reduced hemoglobin, the reflected light can be used to determine oxygenation levels. The signal travels through the fiber 52 and the optical extension tube 26 which is connected to the detecting photocell assembly and oxygen saturation computer (not shown). Thus, the oxygen saturation computer monitors and records the oxygen saturation of the blood flowing past the catheter tip 54. A conventional system used for this particular application is the Opticath oximeter manufactured by Oximetrix, Inc.

A thermistor 39 is located on the distal portion of a bifilar wire 51 located in the lumen 48. The thermistor 39, made of semiconductors whose resistance varies with temperature, is used to monitor a patient's core body temperature. The thermistor 39, as shown in FIG. 1, is located near the distal end 11 of the tubular body 16. A pediatric catheter 15 would typically have the thermistor 39 located 2.5 cm from the distal tip 11 of the catheter 15, whereas a catheter 15 used for an adult would have the thermistor 39 located approximately 3.5 cm from the distal tip 11. The length of the insulated wire 58 extending from the proximal end 20 of the pigtail sheath 12 to the location where the thermistor connector 60 attaches to the insulated wire 58 is approximately 35 cm.

The intraarterial and intraventricular signals are monitored and the pacemaker pulse is generated via a plurality of electrodes 62, 64, 66 spaced between the proximal end 18 and distal end 11 of the tubular body 16 of the catheter 15. Although the illustrated embodiment includes three pairs of electrodes, the number and location of the electrodes can be varied widely depending upon the intended use of the catheter, as will be appreciated by one of skill in the art.

The cardiac catheter electrodes 62, 64, 66 of the present invention are manufactured in accordance with the following steps. For convenience, the construction of only a single electrode band will be described in detail herein.

Figure 3:
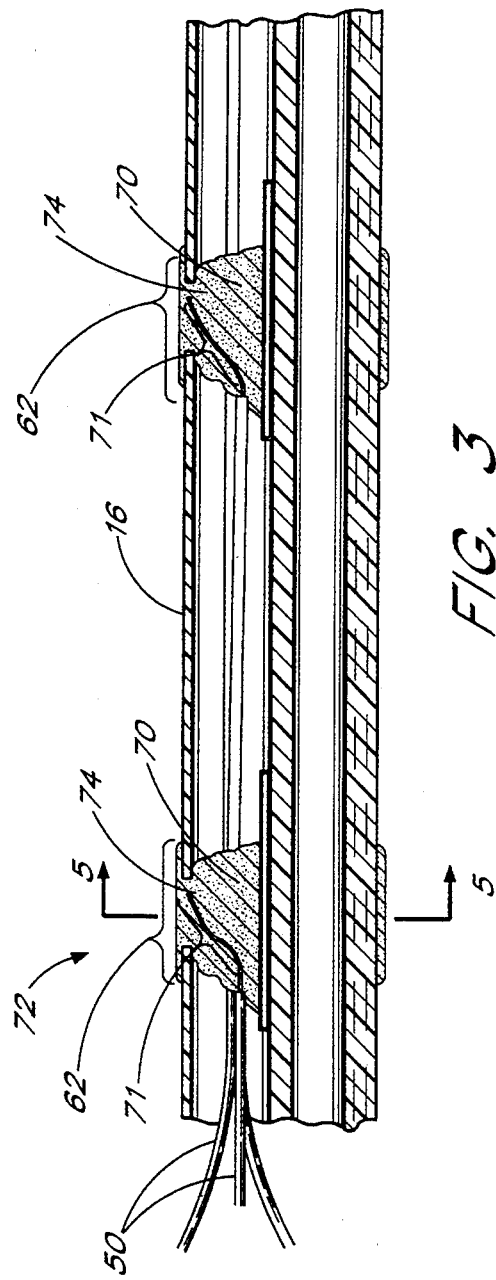
FIG. 3 is a side elevational cross sectional view ore the cardiac catheter illustrating the electrodes of the present invention.

An insulated cable 63, which houses a plurality of wires 50 and connects to medical instruments and equipment, is threaded through or molded within the pigtail sheath 12, and the wires 50 are positioned within the lumen 48 of the flexible tube 16, in accordance with known techniques. As shown in FIG. 3, at least the distal end 70 of the wire 50 is un-insulated, thereby providing an exposed electrical contact 71 for the corresponding electrode 62.

An opening 72 is made in the sidewall of the tubular body 16 for exposing an electrical contact where the electrode 62 is to be located. Depending upon the thickness of the electrode band, the opening 72 can be positioned at the bottom of a shallow annular recess around the circumference of the tubular body 16. In this manner, the outer diameter of the electrode band can be substantially the same as that of the adjacent tubular body.

Electrical contact between the contact 71 and the electrode band can be accomplished in any of a variety of ways. In one embodiment, the electrical contact 71 is positioned sufficiently close to the surface of the tubular body 16 that application of the conductive electrode band will contact the electrical contact 71 directly. This may be accomplished by co-extruding the tubular body 16, with the electrical contact 71 appropriately positioned therein. Alternatively, the tubular body is extruded with an electrical contact lumen, and the electrical contact 71 is positioned close to the radially outwardmost side wall of the lumen.

Preferably, however, a conductive material is positioned between the electrical contact 71 and the electrode band 71, as illustrated in FIG. 3. Suitable materials include any electrically conductive material that is sufficiently formable to permit introduction into the lumen for contacting electrical contact 71 and conforming to fill the space between the contact 71 and the electrode band. Preferably, the material is hardenable from a first, relatively conformable state to a second, relatively solid state. Compounds having these characteristics will be referred to herein collectively as electrically conductive adhesives, and some preferred species will be discussed infra.

Referring to FIG. 3, the exposed electrical contact 71 is aligned with the opening 72 and a conductive adhesive 74 is injected into the opening 72. The conductive adhesive 74 surrounds and attaches to the exposed electrical contact 71 and fills the lumen beneath the hole 72. The electrode 62 is thereafter placed in electrical communication with the exposed electrical contact 71 by means of the conductive adhesive 74.

Figure 4:
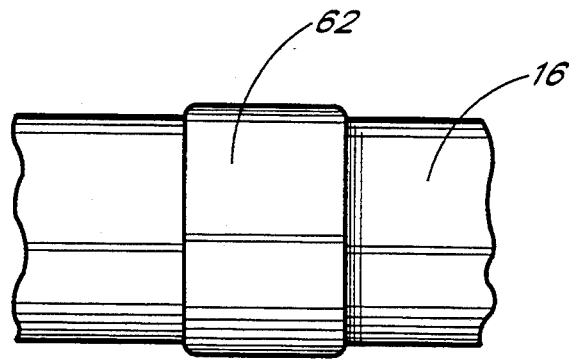
FIG. 4 is a side view of the present invention showing an electrode circumscribing the catheter body. The profile of the electrode is exaggerated for the purpose of illustration.
Figure 5:
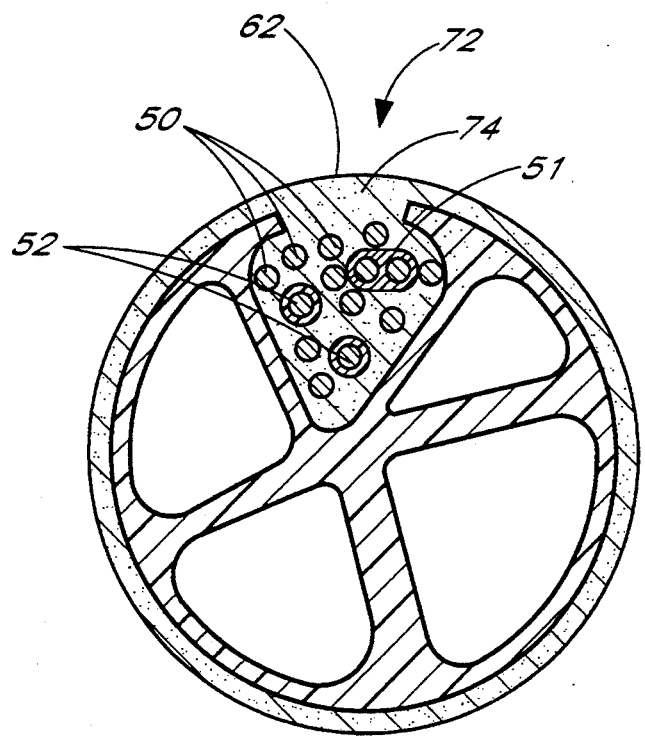
FIG. 5 is a cross section taken along the line 5—5 of FIG. 3, illustrating the components of the cardiac catheter and, in particular, the electrodes of the present invention.

As shown in FIGS. 3, 4 and 5, the electrode 62 is applied to the exterior surface of the tubular body 16 as an adhesive conductive layer rather than as a preformed metal band. The conductive adhesive electrode band 62 preferably extends in an annular ring around the tubular body 16 at the location of the exposed electrical contact 71. However, other symmetrical or asymmetrical electrode configurations can be produced as desired for a particular application.

The electrode 62 may be applied to the surface of the tubular body 16 in any of a variety of ways, including masking and spraying, brushing, or dipping operations. For some metals and metallic materials, spotter coating, vapor phase deposition or liquid phase deposition techniques can also be used.

Thus, the conductive adhesive electrode 62 band presents a relatively smooth surface that is substantially continuous with the external surface of the catheter 15. In addition, due to the thin wall thickness of the adhesive band, there are essentially no sharp edges on the electrode band 62 which could snag or scrape against the walls of an artery, a vein or a patient's heart and possibly become detached from the catheter 15. In one particular embodiment, electrode 62 was brush painted onto the tubular body 16 in an annular band having an axial length of about 2–5 mm and a layer thickness of about 12$\mu$ nominal.

Figure 6:
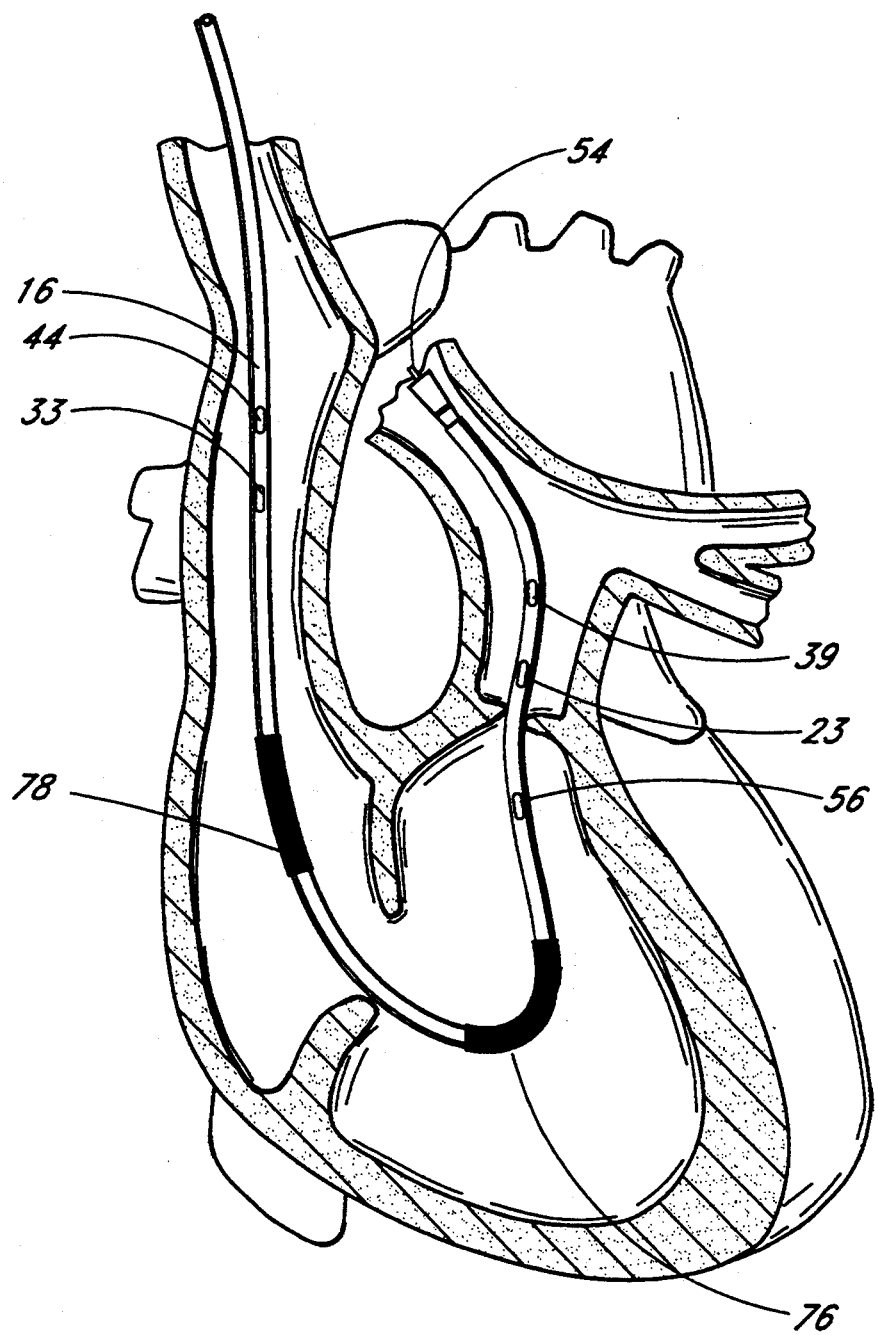
FIG. 6 is a cross section of the heart illustrating the placement of the cardiac catheter comprising an alternate embodiment of the electrodes of the present invention within the chambers of the heart.

In another embodiment of the present invention, tile catheter 15 comprises two relatively elongated electrodes. As shown in FIG. 6, one electrode 76 is located near the distal end 11 of the tubular body 16 and the other electrode 78 is spaced apart proximally on the tubular body 16. The electrodes are positioned such that the proximal electrode 78 is located in the right atrium at the same time that the distal electrode 76 is located in the right ventricle. The optimal axial distance between the two electrodes 76, 78 will be well known by one of skill in the art for any particular anatomical setting. For convenience, the construction of only a single electrode band will be discussed in detail herein.

As with the previous embodiment of the present invention, the electrode 76 is applied to the exterior surface of the tubular body 16 as an adhesive conductive layer rather than as a preformed metal band. The conductive adhesive electrode band 76 preferably extends in a continuous annular ring around the tubular body at the location of the exposed electrical contact 71.

In this embodiment, the electrode 76 has an axial length of greater than about 2 cm and preferably from about 5–10 cm. The electrode 76 has a layer thickness of about 12$\mu$ nominal, although layer thickness may vary depending upon the particular conductive adhesive used and the application technique. The extended length of the electrode 76 increases the probability that the electrode 76 will come in contact with the wall of the chamber of the heart. An added benefit to this particular electrode 76 configuration is its relatively high flexibility compared to conventional preformed band electrodes. Preformed band electrodes cannot provide the flexibility and thin-wall thickness of the present invention.

In addition, since this particular embodiment of the present invention employs only two elongate electrode 76, 78, one can advantageously reduce the number of wires 50 in the lumen 48 of the tubular body 16. Subsequently, the overall diameter of the tubular body 16 of the catheter 15 may be reduced.

Other embodiments employing various combinations of the above mentioned electrodes 76,78 may also be used. Such combinations include: a 5 cm distal electrode and a 10 cm proximal electrode, or a 10 cm distal electrode and a 5 cm proximal electrode. Other configurations may also include combinations of elongate electrodes with smaller band electrodes. For example, a 10 cm distal electrode may be used in combination with two 2 mm proximal electrodes.

Referring back to FIGS. 3, 4 and 5, a variety of biocompatible conductive adhesive 74 materials may be used to electrically connect the electrode 62 to the exposed electrical contact 71. The base material may consist of an epoxy or thermoplastic material. A conductive adhesive such as electrically conductive material #113-37, manufactured by Conductive Materials, Inc., has been found to work particularly well for this application. Other materials, such as Dupont 5008 manufactured by Dupont, may also be used. Suspended within the base are fine particles of conductive materials, such as gold, silver, carbon, etc. Due to the conductive materials suspended within the epoxy, adequate electrical contact is made between the wire 50 and the outer surface of the tubular body 16.

The conductive adhesive 74 adheres to the uninsulated portion of the wire 50 and the inside walls of the lumen 48 exposed by the opening 72 in the tubular body 16, and may be trimmed or polished so that it is flush to the external surface of the tubular body 16. This ensures that the wire 50 will remain embedded and in contact with the conductive adhesive 74, in spite of the degree and location of flexing of the tubular body 16. In addition, the conductive adhesive 74 completely seals the opening 72 in the tubular body 16, thereby preventing any fluids from entering the lumen 48 and contaminating the catheter 15 or creating shorts within the catheter 15.

The appropriate electrical contact 71 and flexible tube 16 materials are preferably chosen in order to further insure secure attachment of the conductive adhesive electrode band 62 to the electrical contact 71. A #38 gauge nickel wire, made by California Fine Wire, has been found to work well in the present invention, although any gauge of wire 50 within the range of #36-#40 would also be appropriate. Other materials, such as insulated copper magnet wire, also meet the surface area and conductivity requirements of the present invention.

The method of manufacturing the conductive adhesive band electrodes 62, 64, 66 permits easier placement of the electrodes 62, 64, 66 onto the flexible tube 16, in contrast to the conventional metal band electrodes. In addition, the electrodes 62, 64, 66 of the present invention are easier to fabricate, highly conductive, strong (i.e not likely to break once complete) and continuous with the surface of the flexible tube 16 (i.e. substantially smooth external profile).

In use, the tubular body 16 of the catheter 15, comprising a plurality of electrodes 62, 64, 66, is inserted into the veins or arteries of a patient and advanced to the chambers of the heart. The electrodes 62, 64, 66 are then properly located against the walls of the heart so that the electric potentials in the walls forming the chambers of the heart can be monitored. In addition, if the patient suffers cardiac arrest during the above mentioned procedure, the pacing electrodes are also able to deliver the appropriate electrical therapy to the heart.

The material and dimensional characteristics of the tubular body 16 of the cardiac catheter 15 are selected based upon the intended application of the catheter. In one embodiment, a 0.105 inch outside diameter PVC tubular body has been found to provide appropriate flexibility and surface characteristics for a pacing catheter. However, the diameter and hardness of the tube may range from 0.090 inch to 0.108 inch and from 90-100 durometer shore "A", respectively, and still readily meet the present inventor's flexibility requirements for this device. If the diameter of the flexible tube 16 is too small, the wires 50 and optical fibers 52 will not fit within the lumen of the catheter 15. If, however, the diameter is too large, the flexible tube 16 may not fit within the veins or arteries of the patient. Therefore, it is important that an appropriately sized diameter flexible tube 16 be used for this device.

The material used to manufacture the tubular body 16 of the cardiac catheter 15 must be biocompatible with a patient's body and provide the appropriate surface characteristics for secure attachment of the conductive adhesive electrode bands 62, 64, 66. In addition, the material preferably exhibits sufficient structural integrity when extruded in the desired dimensions to produce a catheter body having pushability and torqueability characteristics to carry the electrodes to the desired vascular or cardiac site. Such materials are well-known in the cardiovascular catheter arts.

Figure 7:
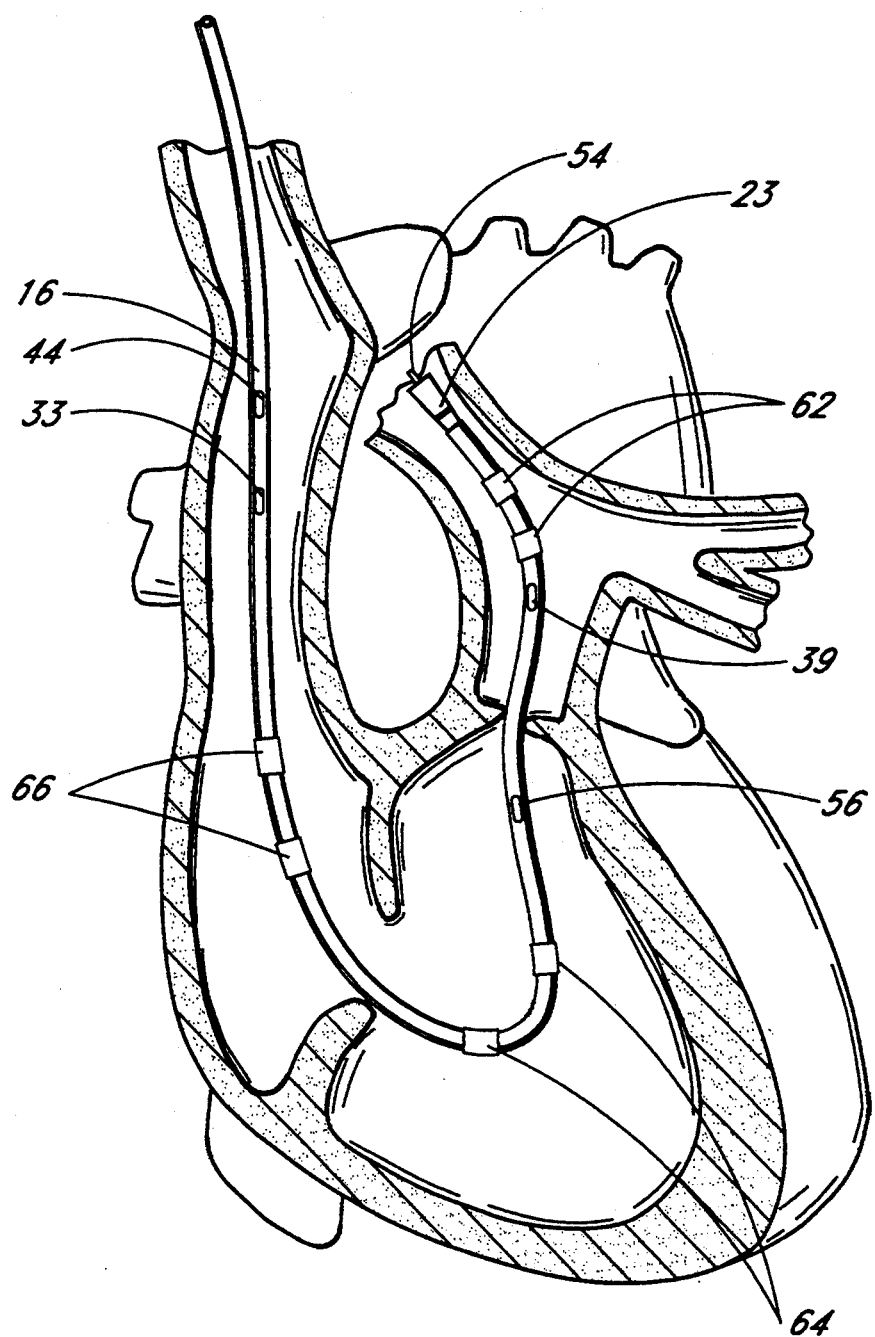
FIG. 7 is a cross section of the heart illustrating the placement of the cardiac catheter within the chambers of the heart.

FIG. 7 is a cross section of the heart illustrating the placement of the cardiac catheter 15 within the chambers of the heart. By placing a plurality of electrodes 62, 64, 66 along the length of the flexible tube 16 of the present invention, multiple electrical measurements may be taken simultaneously.

Numerous variations and modifications can be made without departing from the spirit of the present invention. Therefore, it should be clearly understood that the forms of the present invention described above and shown in the figures of the accompanying drawings are illustrative only and are not intended to limit the scope of the present invention.

What is claimed is:

1. A catheter for conducting an electronic signal within a body lumen, comprising:
   an elongate flexible tubular body, having proximal and distal ends;
   at least one conductor extending axially through the tubular body;
   at least one conductive adhesive electrode on the tubular body in electrical communication with the proximal end of the body by way of said conductor.

2. A catheter as in claim 1, wherein the conductive adhesive electrode extends in an annular ring around the tubular body.

3. A catheter as in claim 1, wherein said electrode is disposed distally of at least one additional, proximal electrode.

4. A catheter as in claim 1, comprising at least two distal electrodes and at least two proximal electrodes on the tubular body.

5. A catheter as in claim 1, wherein the electrode comprises thick film polymeric material.

6. A catheter as in claim 5, wherein the electrode has a thickness of no more than about 0.003 inch.

7. A catheter as in claim 2, wherein the axial length of the annular ring is between about 0.2 and 0.5 cm long.

* * * * *